United States Patent [19]

Nakamura et al.

[11] 4,217,410

[45] Aug. 12, 1980

[54] SILVER HALIDE COLOR PHOTOGRAPHIC LIGHT-SENSITIVE MATERIALS WITH PHOSPHATE SOLVENT

[75] Inventors: Kotaro Nakamura; Akio Mitsui, both of Minami-ashigara, Japan

[73] Assignee: Fuji Photo Film Co., Ltd., Asigara, Japan

[21] Appl. No.: 19,018

[22] Filed: Mar. 8, 1979

[30] Foreign Application Priority Data

Mar. 10, 1978 [JP] Japan ........................ 53-27448

[51] Int. Cl.$^2$ ........................ G03C 1/40; G03C 1/10

[52] U.S. Cl. ........................ 430/546; 430/551

[58] Field of Search ........................ 96/97, 100 R, 56

[56] References Cited

U.S. PATENT DOCUMENTS

| | | | |
|---|---|---|---|
| 2,322,027 | 6/1943 | Jelley et al. | 96/97 |
| 3,676,137 | 7/1972 | Mizuki et al. | 96/56 |
| 3,891,445 | 6/1975 | Arai et al. | 96/100 |
| 4,009,038 | 2/1977 | Arai et al. | 96/56 |

*Primary Examiner*—Richard L. Schilling

*Attorney, Agent, or Firm*—Sughrue, Rothwell, Mion, Zinn and Macpeak

[57] ABSTRACT

A silver halide color photographic light-sensitive material which comprises a support and at least one silver halide emulsion layer on said support, wherein at least one of said emulsion layers contains a hydrophobic phenol type or naphthol type cyan dye forming coupler and at least one coupler solvent represented by the following general formula (I):

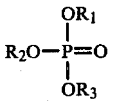

(I)

wherein $R_1$, $R_2$ and $R_3$ each represent a branched chain alkyl group having 8 or more carbon atoms and may be the same or different provided that the sum total of carbon atoms in the molecule is 24 to 40.

12 Claims, No Drawings

SILVER HALIDE COLOR PHOTOGRAPHIC LIGHT-SENSITIVE MATERIALS WITH PHOSPHATE SOLVENT

BACKGROUND OF THE INVENTION

1. Field of the Invention

The present invention relates to silver halide color photographic light-sensitive materials and particularly to silver halide color photographic light-sensitive materials which form stabilized color images.

In greater detail, the present invention relates to a silver halide color photographic light-sensitive material which comprises a support and at least one silver halide emulsion layer on said support wherein at least one of said emulsion layers contains a hydrophobic phenol or naphthol type cyan dye forming coupler and at least one specific alkyl phosphoric acid ester as a coupler solvent and the stability to moisture or heat of the cyan dye images formed upon development is improved.

2. Description of the Prior Art

It has been known that when silver halide photographic light-sensitive materials are subjected to color development after exposure to light, the oxidized aromatic primary amine developing agent reacts with the dye forming couplers to yield indoaniline, indophenol, indamine, phenoxazine, azomethine or analogous dyes, by which color images are formed. In this process, a substractive process is generally used for color reproduction where yellow, magenta and cyan color images which are complementary colors to blue, green and red are formed. Generally, acyl acetamide type couplers are used to form yellow images, pyrazolone type couplers are used to form magenta images and phenol type or naphthol type couplers are used to form cyan images.

Conventionally, a hydrophobic photographic additive {for example, an oil-soluble coupler, an antioxidant for preventing color stain or color contamination, a color fade preventing agent (e.g., an alkylhydroquinone, an alkylphenol, a chroman, a cumarone, etc.), an oil-soluble filter dye, an oil-soluble ultraviolet absorbing agent, a compound capable of releasing a development inhibitor upon reaction with a developing agent (i.e., a DIR compound, such as DIR hydroquinone, a non-color forming DIR compound, etc.), a developing agent, a dye developing agent, a compound capable of releasing a diffusible dye by self-cleavage upon oxidation under alkaline conditions (i.e., a DRR compound), a compound capable of releasing a diffusible dye upon coupling with a color developing agent (i.e., a DDR coupler), and the like} is dissolved in an appropriate organic solvent having a high boiling point, dispersed in an aqueous solution of a hydrophilic organic colloid, in particular gelatin, in the presence of a surface active agent, and the resulting mixture is incorporated in a hydrophilic organic colloid layer, for example, a light-sensitive emulsion layer, a filter layer, a backing layer, an antihalation layer, an intermediate layer, a protective layer, and the like.

In such cases, a phthalic acid ester compound and an aryl phosphoric acid ester compound are particularly useful as the high boiling point organic solvent. These solvents are used in producing most color and black-and-white light-sensitive photographic materials as solvents for photographic additives (such as an oil-soluble incorporated type coupler, etc.). These solvents are described, for example, in U.S. Pat. Nos. 2,332,027, 2,533,514, 3,287,134, 3,748,141 and 3,779,765, German Pat. No. 1,152,610, British Pat. No. 1,272,561, German patent application (OLS) No. 2,629,842, etc. The high boiling point organic solvents of the phthalic acid ester and the phosphoric acid ester type are widely used due to their ability to disperse couplers, their affinity for a gelatin colloid layer, their influence on the stability of the color image formed, their influence on the hue of the color image formed, their chemical stability in photographic light-sensitive materials, their low price, and the like.

However, these high boiling point organic solvents do not always fulfill all the requirements such as dispersion capability for substantially water-insoluble photographic additives, affinity for an organic hydrophilic colloid layer, influence on the photographic properties, chemical stability in the photographic light-sensitive materials, and the like.

For example, some organic solvents having a high boiling point have a bad influence upon photographic properties (for example, they may cause light fading or fading in the dark of the color images obtained upon development), though they have good dispersibility, sometimes some solvents have properties opposite to the above described properties.

There are cases that color photographs are stored or displayed under exposure to light depending upon their intended use (for example, sometimes they are displayed by exposure to very intense light, such as in the case of exhibition of G-color print films, exhibition of color printing paper or exhibition of color slides, etc. and there are cases when they are stored under comparatively mild conditions) and cases when they are stored in the dark for a long period of time while the period of time in which they are exposed to light is short (for example, color positive films for movies, color printing paper stored in albums, color slides and color negative films, etc.). Fading under the latter storage conditions is caused by moisture in the atmosphere or chemical substances present in very small amounts and by heat. This fading is called fading in the dark or thermal fading, which is distinguished from light fading which occurs under the former conditions. It is well known that dark-thermal fading of cyan images is a particularly more serious problem than that of yellow images or magenta images. This remarkable dark-thermal fading of cyan images becomes a large obstacle to using the color photographs as recording materials for semipermanent preservation. Even if the degree of fading of cyan images is low, the fastness of the cyan images is not balanced with that of the yellow images and that of the magenta images. Consequently, since the color balance deteriorates, it is necessary to increase the fastness of cyan images to that of other color images.

As means for preventing the dark-thermal fading of cyan images, various processes have been known. For example, there are processes which comprise processing color photographs with a stabilizing bath containing hydantoin compounds described in U.S. Pat. No. 2,579,436, carbohydrazides described in U.S. Pat. No. 3,201,244, tetramethylol cyclic alcohols described in U.S. Pat. No. 2,983,607, sugars and aminoacid derivatives described in U.S. Pat. Nos. 3,095,302 and 3,291,606, cysteine described in U.S. Pat. No. 3,201,243, polymethylol compounds described in U.S. Pat. No. 3,473,929, organic ferro-printing preventing agents (mercaptans and tautomers thereof, selenoalcohols and imino group containing heterocyclic compounds) described in Japanese Patent Publication No. 18257/73 or compounds described in U.S. Pat. Nos. 3,676,136 and 3,666,468 and 3,336,135. In these processes, however, not only is the improvement in the fastness of the cyan images insufficient, but also the compounds must be added in a large amount corresponding to about 0.5 to 20% by weight of the processing bath. Therefore, in the color photographs obtained by these processings, the surface of the films becomes sticky and causes undesirable problems, for example, adhesion when applied on an album. Further, through a process which comprises adding compounds described in Japanese Patent Publication No. 32728/73 to an emulsion layer has been proposed, the same effect as that in the processes using the stabilizing bath is obtained.

Since it is generally believed that couplers remaining in an unreacted state in the developed color photographs accelerate the fading of color images, processes which comprise removing the residual couplers have been proposed. For example, there is a process which comprises removing unreacted couplers from layers by diffusion, by splitting the couplers into low molecular fragments during the development processing (British Pat. Nos. 843,940 and 849,065) or a process which comprises dispersing water soluble couplers having a water solubilizing group on the coupling position thereof in emulsion layers in order to protect the dyes formed by development from the influence of the couplers and adding further a dispersion of a hydrophobic solvent which does not have a solvent function to the couplers but has a high solvent function to the dyes formed to the emulsion layers (U.S. Pat. No. 3,271,152).

However, in the former process, an additional processing bath for splitting the couplers into low molecular fragments is required and, in the latter process, there is complexity in the production step that the couplers and the hydrophobic solvent should be dispersed in the emulsion layers respectively. Accordingly, it is difficult to say that both of them are practical processes.

Further, as described in U.S. Pat. No. 3,614,839 and British Pat. Nos. 1,167,519 and 1,151,771, there are processes for improving the fastness of color images which comprise laminating color photographs with a transparent polymer film such as a polystyrene or polyethylene film after development. However, in these processes, not only much labor is involved in laminating but also a small effect is obtained for improving dark-thermal fading of cyan images.

On the other hand, as processes for improving dark-thermal fading of cyan images, processes described in Japanese patent applications (OPI) Nos. 161236/75, 26036/76 and 26037/76 have been proposed, where the coupler solvents are investigated. In these processes, however, not only is a sufficient effect not obtained for improving fastness of cyan images but also the coupler solvents do not always have satisfactory properties in their ability to disperse the oil-soluble couplers or their affinity for the hydrophilic colloid.

Incorporation of alkyl phosphoric acid esters in color photographic light-sensitive materials has been proposed in, for example, U.S. Pat. No. 3,676,137. However, the proposed invention is clearly different from the present invention, because alkyl phosphoric acid esters are used as coupler solvents for 5-pyrazolone type magenta couplers. Further, as described above, since the fastness to light, heat and moisture of magenta images is quite different from that of cyan images, different approaches are required respectively for preventing fading.

Further, in U.S. Pat. No. 4,009,038, a process which comprises dispersing phenol type or naphthol type cyan couplers and 2-(2'-hydroxyphenyl)benzotriazole compounds using dioctylbutyl phosphate has been proposed. This process, however, is very difficult to apply to photosensitive materials, because the emulsified dispersions have very low stability. Further, the invention in this patent application is clearly different from the present invention, because only dioctylbutyl phosphate is described and no experiment is described in said patent application.

Moreover, in U.S. Pat. No. T 969,005, a process which comprises dispersing a yellow coupler, a magenta coupler or a cyan coupler using trinonylphosphate or tridecylphosphate is disclosed. However, it has not been described in this patent application what effect can be obtained when the cyan coupler is dispersed using compounds having a branched carbon chain in the nonyl group or the decyl group.

SUMMARY OF THE INVENTION

Accordingly, the first object of the present invention is to provide photographic light-sensitive materials in which hydrophobic phenol type or naphthol type cyan dye forming couplers are incorporated as dispersions using coupler solvents having good dispersibility for hydrophilic organic colloids.

A second object of this invention is to provide photographic light-sensitive materials which are produced using coupler solvents which do not have a bad influence upon photographic properties such as fogging, sensitivity or maximum image density, etc.

Another object of this invention is to provide color photographic light-sensitive materials which are produced using coupler solvents by which fading in the dark and thermal fading of photographic color images, particularly, cyan images are improved.

Still another object of this invention is to provide a process for improving the fastness of color images easily and effectively.

A still further object of this invention is to provide a process for obtaining color images which have a good color balance even when they are stored for a long period of time after development.

As the result of many studies in order to attain the above described objects, it has been found that these objects can be attained by incorporating hydrophobic phenol type or naphthol type cyan couplers and at least one of the compounds represented by the following general formula (I) in the same silver halide emulsion layer.

DETAILED DESCRIPTION OF THE INVENTION

In the present invention, the compounds represented by the following general formula (I) function to stabilize the cyan couplers to dark-thermal fading. Accordingly, it should be noted that these compounds must be incorporated in the silver halide emulsion layer as a coupler solvent for the cyan couplers.

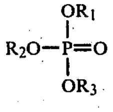

(I)

In the formula (I), $R_1$, $R_2$ and $R_3$ each represent a branched chain alkyl group, and $R_1$, $R_2$ and $R_3$ may be the same or different, wherein the number of carbon atoms included in each of said three alkyl groups is 8 to 24, but the sum total of carbon atoms in $R_1$, $R_2$ and $R_3$ is 24 to 40.

Examples of the branched chain alkyl groups used herein include

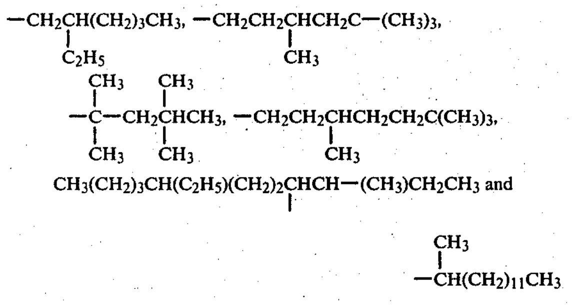

In cases where the alkyl groups are straight chain or the sum total of the number of carbon atoms is less than 24 or more than 40, and cyan couplers are dispersed using the alkyl phosphoric acid esters represented by the general formula (I), the resulting dispersion has low stability and sometimes causes poor color formation or problems occur on coating.

Further, it is particularly preferred in this range that $R_1$, $R_2$ and $R_3$ are each a branched alkyl group having 8 to 10 carbon atoms.

Compounds in which any of $R_1$, $R_2$ and $R_3$ represents an aromatic group do not show the effect of the present invention because they cause high fogging and have a poor effect on preventing dark-thermal fading of cyan images. Considering the fact that even aryl esters of phosphoric acid, dioctylbutyl phosphate, tri-(n-octyl)-phosphate and tri-(n-decyl)phosphate used hitherto as good coupler solvents, which are compounds of analogous chemical structure, do not show a satisfactory result with respect to the objects of the present invention, it is very surprising that the compounds of the present invention show the effect. Accordingly, it is quite unexpected that the objects of the present invention can be attained using branched chain alkyl phosphates.

The compounds represented by the general formula (I) decompose to form hydrolysis products when they are subjected to high temperatures in synthesis. It has been found that these hydrolysis products contribute to the dark-thermal fading of the color images formed by the phenol type or naphthol type cyan couplers. Namely, when the compounds represented by the general formula (I) containing oxidized substances are used as the coupler solvent, the hydrolysis products cause dark-thermal fading of the cyan images formed and impede exhibition of the remarkably excellent effect of improving the dark-thermal fading property of the cyan images which is originally shown by the compounds represented by the general formula (I).

Accordingly, in order to attain the objects of the present invention, it is preferred to use compounds represented by the general formula (I) having an acid value of 5 or less. The acid value is a measure of the amount of hydrolysis product impurities included in the oil, and is measured in accordance with Japanese Industrial Standard JIS K8004. Namely the method of measuring the acid value comprises sampling 1 g of sample, titrating by potassium hydroxide and weighing the potassium hydroxide required for neutralization as a solid. The acid value is a milligram number. There is a tendency for the acid number to become higher as the number of carbon atoms increases because higher temperatures are required for purifying the compound as the number of carbon atoms increases.

In order to attain the objects of the present invention, an acid number of 1 or less and particularly 0.1 or less in the compounds represented by the general formula (I) is preferred.

Examples of the branched chain alkyl phosphates suitably used in the present invention are set forth below. However, the scope of the present invention is not limited to these examples.

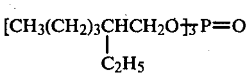

(I-1)

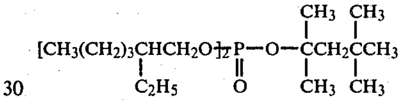

(I-2)

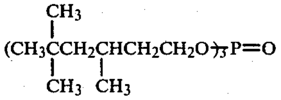

(I-3)

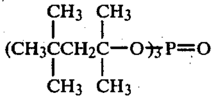

(I-4)

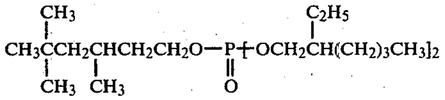

(I-5)

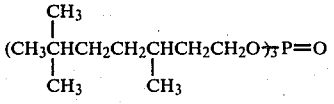

(I-6)

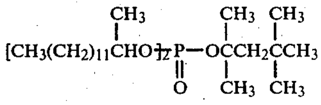

(I-7)

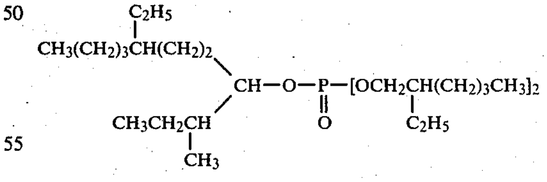

(I-8)

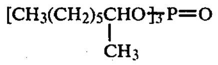

(I-9)

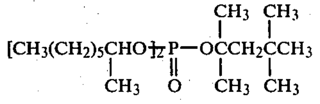

(I-10)

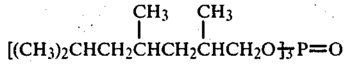

(I-11)

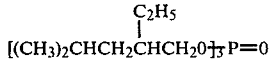

(I-12)

The phosphoric acid esters of the present invention can be produced by the reaction of phosphorus oxychloride with alcohol as described in "Phosphorous and its Compounds" by J. R. Van Wazer, Vol. 2, p. 1221. In this case, a base is used in order to remove by-produced hydrogen chloride. This neutralization operation is carried out strictly so that branched chain alkyl phosphates having a low acid value are produced. After neutralization, the product is thoroughly washed with water in order to remove the salt produced. Further, it is necessary for obtaining branched chain alkyl phosphates having a low acid value that the water content of the crude product is reduced to less than 1% before purification by distillation.

SYNTHESIS EXAMPLE 1

Synthesis of tri-(2-ethylhexyl)phosphate (Compound I-1)

A solution composed of 429.8 g (3.3 mols) of ethylhexyl alcohol, 237.3 g (3 mols) of pyridine and 500 ml of chloroform was cooled with stirring. To this solution, 153.4 g (1 mol) of phosphorus oxychloride was added dropwise to carry out the reaction. After conclusion of the reaction by refluxing for 2 hours with heating, the solution was washed well with water, a diluted aqueous solution of caustic soda and water in turn, and dried by anhydrous sodium sulfate. After the solution was filtered and condensed under a reduced pressure, it was distilled to obtain 392.9 g of tri-(2-ethylhexyl)phosphate (Yield: 90.4%). b.p.: 183°-7° C./1 mmHg.

Synthesis Example 2

Synthesis of tri-(3,5,5-trimethylhexyl)phosphate (Compound I-3)

A solution composed of 476.1 g (3.3 mols) of 3,5,5-trimethyl hexanol, 237.3 g (3 mols) of pyridine and 600 ml of chloroform was cooled with stirring. To this solution, 153.4 g (1 mol) of phosphorus oxychloride was added dropwise (for 15 minutes) while cooling the solution. After addition, the solution was refluxed for 2 hours with heating. After the reaction solution was processed in the same manner as in Synthesis Example 1, it was distilled under vacuum to obtain 411.9 g (Yield: 86.4%) of tri-(3,5,5-trimethylhexyl)phosphate as a fraction having a b.p. 145°-160° C./$2\times10^{-2}$-$3\times10^{-2}$ mmHg.

Synthesis Example 3

Synthesis of tri-(2-ethylhexyl)phosphate having low acid value (Compound I-1)

A solution composed of 429.8 g (3.3 mols) of 2-ethylhexyl alcohol, 237.3 g (3 mols) of pyridine and 500 ml of chloroform was stirred and cooled to −5° C. To this solution, 153.4 g (1 mol) of phosphorus oxychloride was added dropwise at less than 10° C. to carry out the reaction. After conclusion of the reaction by refluxing for 2 hours with heating, 10 times by volume of water was added to the mixture and the oil layer was sufficiently washed with water. It was then washed with a 5% aqueous solution of sodium bicarbonate till the pH of the aqueous layer came to the range of 7.0±0.2. The oil layer was separated and allowed to stand for a night to dry by adding anhydrous sodium sulfate. After this solution was filtered and condensed under a reduced pressure, it was rapidly distilled. A fraction of b.p. 180°-205° C./1.5 mmHg was collected and distilled again. Thus, 369.4 g (Yield: 85.0%) of tri-(2-ethylhexyl)phosphate was obtained. b.p.: 183°-7° C./1 mmHg. The acid value measured according to JIS K8004 was 0.09.

Though the branched chain alkyl phosphoric acid esters represented by the general formula (I) can be used in any ratio to the hydrophobic cyan couplers, a preferred ratio is from about 0.05 to 10 (ratio by weight) and particularly from about 0.1 to 2. A suitable amount of the cyan coupler is about $2\times10^{-3}$ mol to about $5\times10^{-1}$ mol, preferably $1\times10^{-2}$ mol to $5\times10^{-1}$ mol, per mol of silver. When coated on a support the cyan coupler is coated in an amount of about 0.05 to 2.5 g/m$^2$, preferably 0.1 to 1.6 g/m$^2$. When coated on a support the alkyl phosphoric acid ester is coated in an amount of about 0.01 to about 1.0 g/m$^2$, preferably 0.05 to 0.3 g/m$^2$. A weight ratio of alkyl phosphoric acid ester to the hydrophilic colloid, e.g., gelatin, is about 0.01 to 0.6, preferably 0.05 to 0.4.

To incorporate cyan couplers into a silver halide emulsion layer, the cyan coupler is dissolved in the alkyl phosphoric acid esters defined above and optionally a conventional coupler solvent and the resulting solution is dispersed in a hydrophilic colloid such as gelatin. The resulting dispersion is then incorporated into a silver halide emulsion. The alkyl phosphoric acid esters of the present invention can be used in combination with conventional solvents described layer. In this case, the alkyl phosphoric acid esters represented by the general formula (I) is used in an amount of about 30% by weight to 100% by weight, preferably 50 to 100% by weight of the total solvent.

The hydrophobic couplers used in the present invention are non-diffusible couplers soluble in the organic solvents used in adding couplers to emulsion layers of color photographic light-sensitive materials. Namely, as described in the following, the couplers must be non-diffusible, because the couplers must first be dissolved in an organic solvent in order to emulsify and disperse them and the couplers added should be fixed in the emulsion layers. Accordingly, the couplers include those wherein groups containing hydrophobic residue having 8 to 32 carbon atoms are introduced into the coupler molecule. This residue which is called a ballast group is linked directly to the coupler skeleton structure or through an amino bond, an ether bond, a carbonamido bond, a sulfonamido bond, a ureido bond, an ester bond, an imido bond, a carbamoyl bond or a sulfamoyl bond.

Examples of the ballast groups including the following.

(I) Alkyl groups and alkenyl groups:

For example, $-CH_2-(CH_2)_3-(C_2H_5)_2$, $-C_{12}H_{25}$, $-C_{16}H_{33}$ and $-C_{17}H_{33}$.

(II) Alkoxyalkyl groups:

For example, $-(CH_2)_3$-O-$(CH_2)_7CH_3$ and

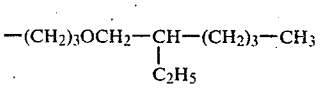

as described in Japanese Patent Publication No. 27563/64.

(III) Alkylaryl groups:

For example,

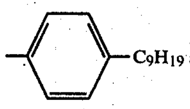
and
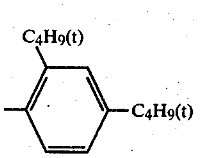

(IV) Alkylaryloxyalkyl groups:
For example,

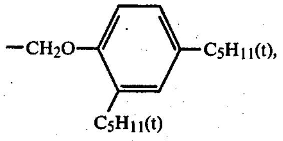

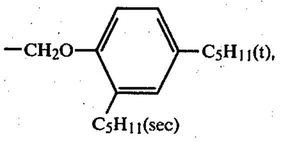

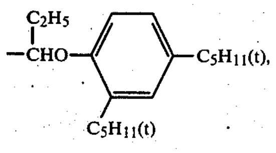

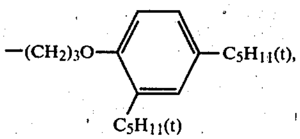

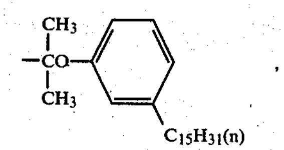

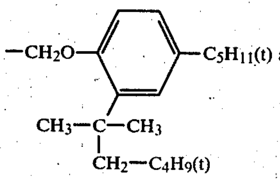
and

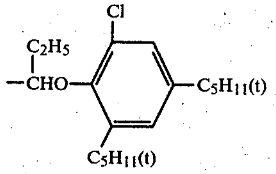

(V) Acylamidoalkyl groups:
For example, groups described in U.S. Pat. Nos. 3,337,344 and 3,418,129 such as

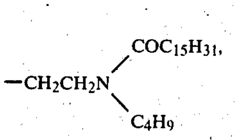

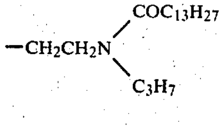
and

-continued

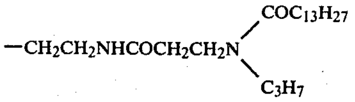

(VI) Alkyloxyaryl groups and aryloxyaryl groups:
For example,

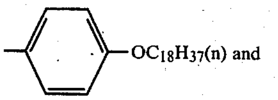
and

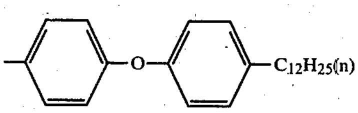

(VII) Alkyl groups substituted by an ester group:
For example,

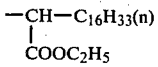
and
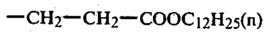

(VIII) Alkyl groups substituted by an aryl group or a heterocyclic group:
For example,

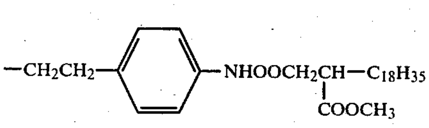

and
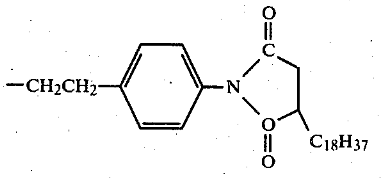

As the hydrophobic cyan couplers suitable for the present invention, there are hydrophobic phenol type and naphthol type couplers described in, for example, Japanese Patent Publication No. 27563/64, British Patent No. 562,205, U.S. Pat. Nos. 2,474,293, 2,895,826, 3,582,322, 2,908,573, 3,476,563, 3,619,196, 2,423,730, 2,801,171, 3,046,129, 3,516,831, 3,311,476, 3,253,294, 3,458,315, 3,227,550, 3,419,390, 3,034,892, 2,772,162, 2,322,027, 3,779,763, 3,632,347, 3,652,286 and 3,591,383 and German Patent Application (OLS) No. 2,207,468.

The phenol type and naphthol type cyan couplers used in the present invention include compounds represented by the following general formulas (II) and (III).

General formula (II)

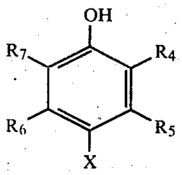

-continued

General formula (III)

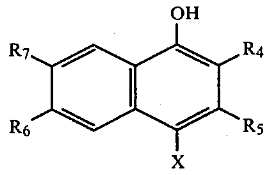

In the formulas, $R_4$ represents a hydrogen atom, an aliphatic group having 1 to 30 carbon atoms (for example, an alkyl ($C_1$–$C_{30}$) group such as a methyl, an isopropyl, a pentadecyl or an eicosyl group), an alkoxy group having 1 to 30 carbon atoms (for example, a methoxy, an isopropoxy, a pentadecyloxy or an eicosyloxy group), a monocyclic aryloxy ($C_6$–$C_{30}$) group (for example, a phenoxy or p-tert-butylphenoxy group), an acylamido group represented by the following formula (IV), a sulfonamido group represented by the following formula (V), a phosphoric acid amido group represented by the following formula (VI), an ureido group represented by the following formula (VII) or a carbamoyl group represented by the following formula (VIII) or (IX):

$$-NH-CO-B \quad (IV)$$

$$-NH-SO_2-B \quad (V)$$

(VI)

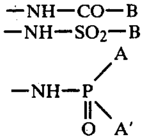

$$-NHCONH-B \quad (VII)$$

$$-CONH-B \quad (VIII)$$

(IX)

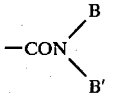

In the formulas, B and B′ which may be the same or different each represent an aliphatic group having 1 to 32 carbon atoms and preferably a straight or branched chain alkyl group or a cyclic alkyl group having 1 to 20 carbon atoms (for example, cyclopropyl, cyclohexyl or norbornyl, etc.) or a monocyclic or bicyclcic aryl ($C_6$–$C_{32}$) group (for example, phenyl or naphthyl, etc.). Here, the above described alkyl group or aryl group may be substituted by a halogen atom (for example, fluorine, chlorine, etc.), a nitro group, a cyano group, a hydroxyl group, a carboxyl group, an amino group (for example, amino, alkylamino, dialkylamino, anilino or N-alkylanilino, etc.), an alkyl group (for example, those which are described in the $R_4$), an aryl group (for example, phenyl or acetylaminophenyl, etc.), an alkoxycarbonyl group (for example, tetradecyloxycarbonyl, etc.), an acyloxycarbonyl group, an amide group (for example, acetamide or methane sulfonamide, etc.), an imide group (for example, saccinimide), a carbamoyl group (for example, N,N-dihexylcarbamoyl, etc.), a sulfamoyl group (for example, N,N-diethylsulfamoyl, etc.), an alkoxy group (for example, ethoxy, tetradecyloxy or octadecyloxy, etc.) or an aryloxy group (for example, phenoxy, p-tert-butylphenoxy, 2,4-diamylphenoxy or 4-hydroxy-3-tert-butylphenoxy, etc.). A and A′ represent each B, —OB, —NH—B or —$NB_2$ wherein B has the same meaning as described above.

$R_4$ may contain substituents conventionally used in addition to the above described substituents.

In the formulas, $R_5$, $R_6$ and $R_7$ represent each a hydrogen atom, a halogen atom, an alkyl group, an aryl group, a straight or branched alkoxy ($C_1$–$C_{30}$) group (for example, methoxy, isopropoxy and pentadecyloxy, etc.), an alkylthio group, a heterocyclic group, an amino group, a carbonamido group, a sulfonamido group, a sulfamoyl group or a carbamoyl group. For example, they represent any of the following:

A hydrogen atom, a halogen atom (for example, chlorine and bromine, etc.), a primary, secondary or tertiary alkyl group having 1 to 22 carbon atoms (for example, methyl, propyl, isopropyl, n-butyl, sec-butyl, tert-butyl, hexyl, dodecyl, 2-chlorobutyl, 2-hydroxyethyl, 2-phenylethyl, 2-(2,4,6-trichlorophenyl)ethyl, 2-amylethyl, iso-$C_3F_7$ and $C_6F_{12}H$—, etc.), a straight or branched alkylthio ($C_1$–$C_{22}$) group (for example, hexadecylthio, etc.), a mono or bicyclic aryl ($C_6$–$C_{30}$) group (for example, phenyl, 4-methylphenyl, 2,4,6-trichlorophenyl, 3,5-dibromophenyl, 4-trifluoromethylphenyl, 2-trifluoromethylphenyl, 3-trifluoromethylphenyl, naphthyl, 2-chloronaphthyl and 3-ethylnaphthyl, etc.), a 5- or 6-membered heterocyclic group having an oxygen atom, a sulfur atom or a nitrogen atom as a hetero atom (for example, a benzofuranyl, furanyl, thiazolyl, benzothiazolyl, naphthothiazolyl, oxazolyl, benzoxazolyl, naphthoxazolyl, pyridyl or quinonyl group, etc.), an amino group (for example, amino, methylamino, diethylamino, dodecylamino, phenylamino, tolylamino, 4-(3-sulfobenzamido)anilino, 4-cyanophenylamino, 2-trifluoromethylphenylamino and benzothiazolylamino, etc.), a carbonamido group {for example, alkylcarbonamido groups such as ethylcarbonamido or decylcarbonamido, etc., aryl carbonamido groups such as phenylcarbonamido, 2,4,6-trichlorophenyl carbonamido, 4-methylphenyl carbonamido, 2-ethoxyphenyl carbonamido, 3-[α-(2,4-di-tert-amylphenoxy)acetamide]benzamido or naphthyl carbonamido, etc. and heterocyclic carbonamido groups such as thiazolyl carbonamido, benzothiazolyl carbonamido, naphthothiazolyl carbonamido, oxazolyl carbonamido, benzoxazolyl carbonamido, imidazolyl carbonamido or benzimidazolyl carbonamido, etc.}, a sulfonamido group {for example, alkyl sulfonamido groups such as butyl sulfonamido, dodecyl sulfonamido or phenylethyl sulfonamido, etc., aryl sulfonamido groups such as phenyl sulfonamido, 2,4,6-trichlorophenyl sulfonamido, 2-methoxyphenyl sulfonamido, 3-carboxyphenyl sulfonamido, or naphthyl sulfonamido, etc. and heterocyclic sulfonamido groups such as thiazolyl sulfonamido, benzothiazolyl sulfonamido, imidazolyl sulfonamido, benzimidazolyl sulfonamido or pyridyl sulfonamido, etc.}, a sulfamoyl group {for example, alkyl sulfamoyl groups such as propyl sulfamoyl, octyl sulfamoyl, pentadecyl sulfamoyl or octadecyl sulfamoyl, etc., aryl sulfamoyl groups such as phenyl sulfamoyl, 2,4,6-trichlorophenyl sulfamoyl, 2-methoxyphenyl sulfamoyl or naphthyl sulfamoyl, etc., and heterocyclic sulfamoyl groups such as thiazolyl sulfamoyl, benzothiazolyl sulfamoyl, oxazolyl sulfamoyl, benzimidazolyl sulfamoyl or pyridyl sulfamoyl, etc.} and a carbamoyl group {for example, alkyl carbamoyl groups such as ethyl carbamoyl, octyl carbamoyl, pentadecyl carbamoyl or octadecyl carbamoyl, etc., aryl carbamoyl groups such as phenyl carbamoyl or 2,4,6-trichlorophenyl carbamoyl, etc. and heterocyclic carbamoyl groups such as thiazolyl carbamoyl, benzothiazolyl carbamoyl, oxazolyl carbamoyl, imidazolyl carbamoyl or benzimidazolyl carbamoyl, etc.}.

In the formulas, X represents a hydrogen atom or a group which is released upon coupling (for example, a halogen atom, a thiocyano group, an acyloxy group, an alkoxy group, an aryloxy group or a cyclic imide group, etc.).

The hydrophobic cyan couplers used for color photographic sensitive materials of the present invention are not limited to the above described general formulas (II) and (III) but can be selected from a wide range. Generally, phenol type compounds are advantageously used as the cyan couplers. In the present invention, at least one kind of hydrophobic cyan couplers is used. That is two or more phenol type or naphthol type compounds may be combined. Further, a combination of the phenol type compound and the naphthol type compound may be used.

In the following, examples of the cyan couplers used in the present invention are shown, but the cyan couplers in the present invention are not limited to these.

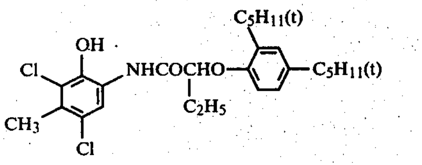
(II-1)

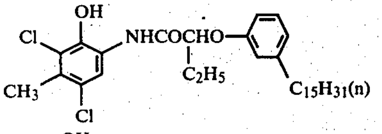
(II-2)

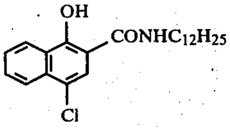
(II-3)

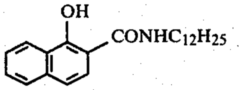
(II-4)

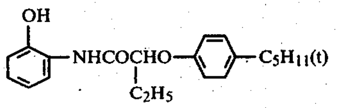
(II-5)

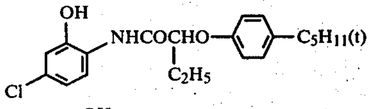
(II-6)

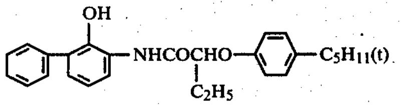
(II-7)

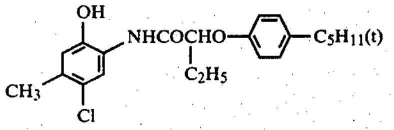
(II-8)

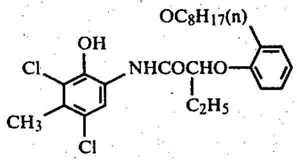
(II-9)

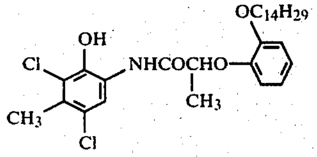
(II-10)

-continued

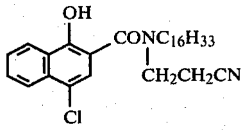
(II-11)

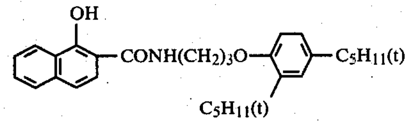
(II-12)

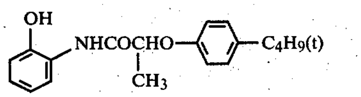
(II-13)

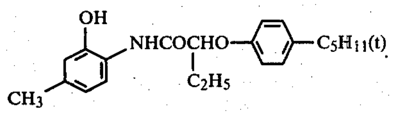
(II-14)

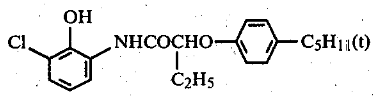
(II-15)

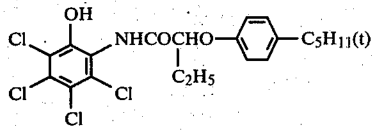
(II-16)

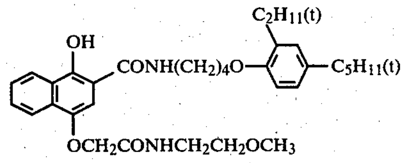
(II-17)

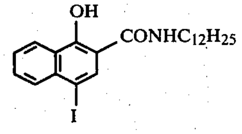
(II-18)

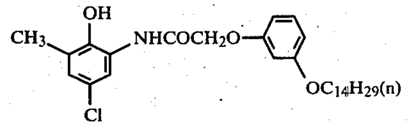
(II-19)

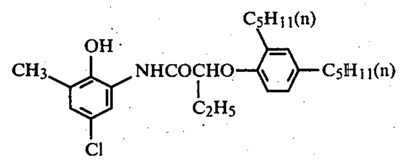
(II-20)

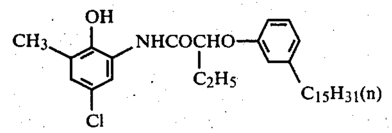
(II-21)

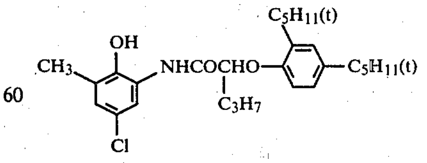
(II-22)

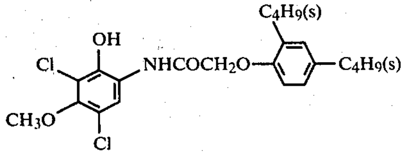
(II-23)

-continued
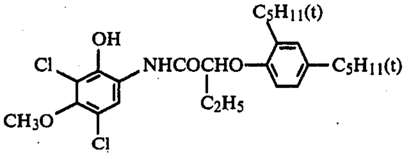
(II-24)
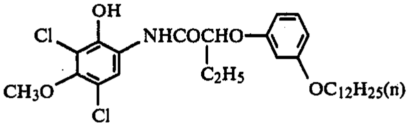
(II-25)
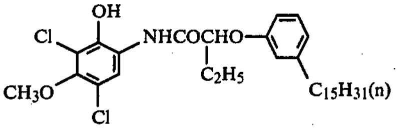
(II-26)
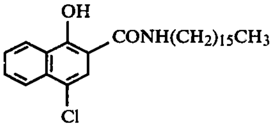
(II-27)
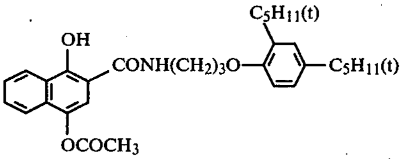
(II-28)
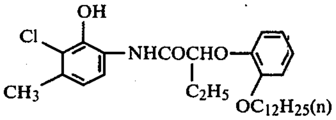
(II-29)
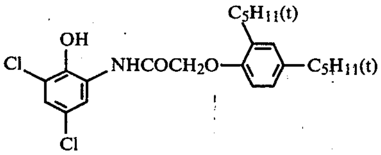
(II-30)
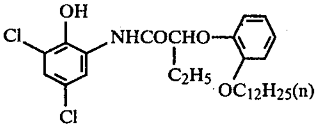
(II-31)
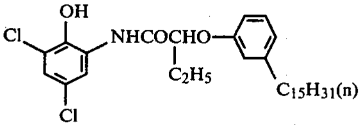
(II-32)
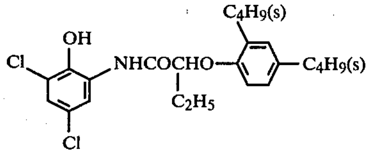
(II-33)
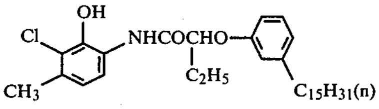
(II-34)
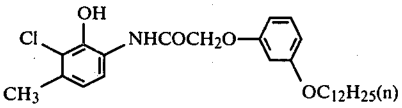
(II-35)
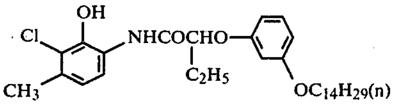
(II-36)
-continued
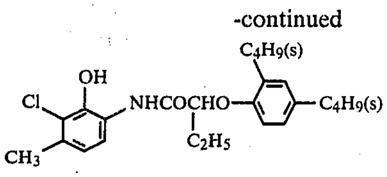
(II-37)
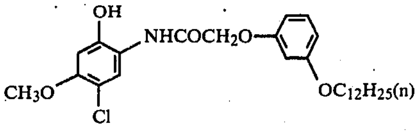
(II-38)
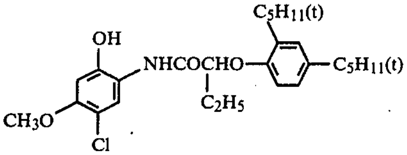
(II-39)
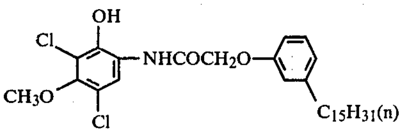
(II-40)
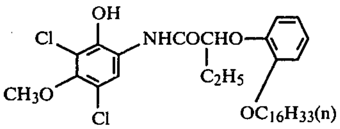
(II-41)
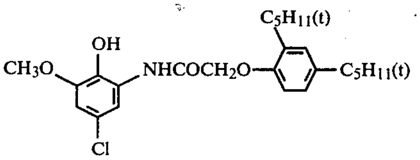
(II-42)
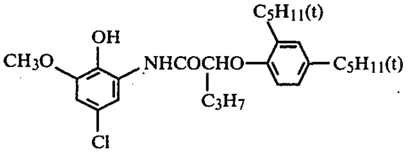
(II-43)
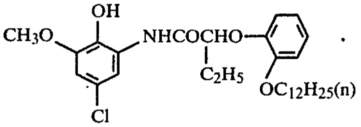
(II-44)
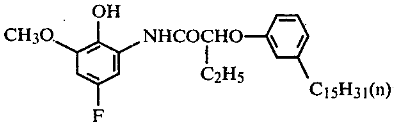
(II-45)
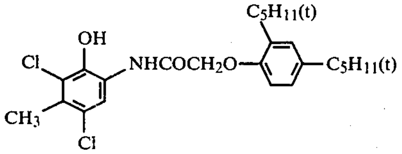
(II-46)
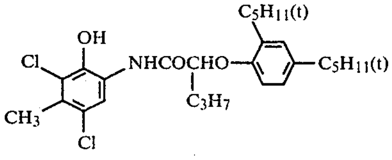
(II-47)
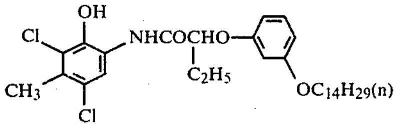
(II-48)

-continued (II-49)

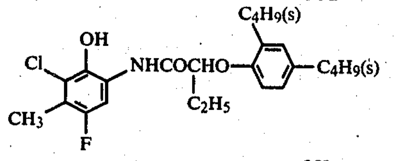

(II-50)

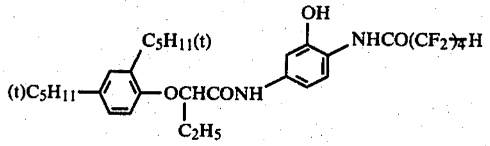

(II-51)

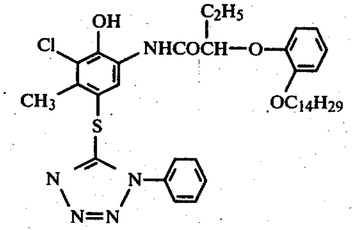

(II-52)

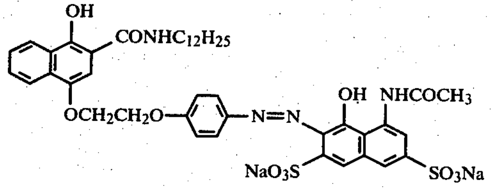

In order to produce color photographic light-sensitive materials by the present invention, it is possible to use well known couplers in addition to cyan forming couplers. As the couplers, non-diffusible ones having a hydrophobic group called a ballast group in the molecule are preferred to use. The couplers may be 4-equivalent or 2-equivalent to silver ion. Further, the couplers may include colored couplers having a color correction effect and couplers which release a development inhibitor by development (the so-called DIR couplers). The couplers may include those which form a colorless product by the coupling reaction.

As yellow forming couplers, known open chain type ketomethylene couplers can be used. Among them, benzoylacetanilide type compounds and pivaloyl acetanilide type compounds are advantageously used. Examples of the yellow forming couplers to be used include these described in U.S. Pat. Nos. 2,875,057, 3,265,506, 3,408,194, 3,551,155, 3,582,322, 3,725,072 and 3,891,445, German Patent No. 1,547,868, German Patent Applications (OLS) Nos. 2,219,917, 2,261,361, and 2,414,006, British Patent No. 1,425,020, Japanese Patent Publication No. 10783/76 and Japanese Patent Applications (OPI) Nos. 26133/72, 73147/73, 102636/76, 6341/75, 123342/75, 130442/75, 21827/76 and 87650/75.

As magenta forming couplers, pyrazolone type compounds, imidazolone type compounds and cyanoacetyl compounds can be used, and pyrazolone type compounds are particularly advantageous. Examples of the magenta forming couplers to be used include substances described in U.S. Pat. Nos. 2,600,788, 2,983,608, 3,062,653, 3,127,269, 3,311,476, 3,419,391, 3,519,429, 3,558,319, 3,582,322, 3,615,506, 3,834,908 and 3,891,445, German Patent No. 1,810,464, German Patent Applications (OLS) Nos. 2,408,665, 2,417,945, 2,418,959 and 2,424,467, Japanese Patent Publications Nos. 6031/65 and 45990/76 and Japanese Patent Applications (OPI) Nos. 20826/76, 58922/77, 129538/74, 74027/74, 159336/75, 42121/77, 74028/74, 60233/75 and 26541/76.

As the colored couplers, it is possible to use substances described in, for example, U.S. Pat. Nos. 3,476,560, 2,521,908 and 3,034,892, Japanese Patent Publications Nos. 2016/69, 22335/63, 11304/67 and 32461/69, Japanese Patent Applications (OPI) Nos. 26034/76 and 42121/77 and German Patent Application (OLS) No. 2,418,959.

As the DIR couplers, it is possible to use substances described in U.S. Pat. Nos. 3,227,554, 3,617,291, 3,701,783, 3,790,384 and 3,632,345, German Patent Applications (OLS) Nos. 2,414,006, 2,454,301 and 2,454,329, British Patent No. 953,454, Japanese Patent Applications (OPI) Nos. 69624/77, 122335/74 and 69624/77 and Japanese Patent Publication No. 16141/76.

The photosensitive materials may contain compounds which release a development inhibitor by development other than DIR couplers. For example, it is possible to use substances described in U.S. Pat. Nos. 3,297,445 and 3,379,529 and German Patent Application (OLS) No. 2,417,914.

Two or more of the above described couplers may be incorporated in the same layer. Further, two or more layers may contain the same compound.

In order to introduce couplers other than the cyan couplers into silver halide emulsion layers, known processes, for example, the process described in U.S. Pat. No. 2,322,027 can be used. For example, they are dispersed in hydrophilic colloids after being dissolved in phthalic acid alkyl esters (for example, dibutyl phthalate or dioctyl phthalate, etc.), phosphoric acid esters (for example, diphenyl phosphate, triphenyl phosphate, tricresyl phosphate or dioctylbutyl phosphate), citric acid esters (for example, tributyl acetylcitrate), benzoic acid esters (for example, octyl benzoate), alkylamides (for example, diethyllaurylamide) or organic solvents having about 30° C.–150° C. of the boiling point such as lower alkyl acetates such as ethyl acetate or butyl acetate, ethyl propionate, secondary butyl alcohol, methyl isobutyl ketone, $\beta$-ethoxyethyl acetate or methyl cellosolve acetate, etc. The above described organic solvents having a high boiling point and the organic solvents having a low boiling point may be used as a mixture of them.

In cases that the couplers have acid groups such as carboxylic acid group or sulfonic acid group, they are introduced into the hydrophilic colloids as an alkaline aqueous solution.

These couplers are generally added in an amount of $2\times10^{-3}$ to $5\times10^{-1}$ mols and preferably $1\times10^{-2}$ to $5\times10^{-1}$ mols per 1 mol of silver in the emulsion layers.

The photographic emulsions used in the present invention may be spectrally sensitized by methine dyes or others. As dyes to be used, there are cyanine dyes, merocyanine dyes, composite cyanine dyes, composite merocyanine dyes, holopolar cyanine dyes, hemicyanine dyes, styryl dyes and hemioxonol dyes. Particularly useful dyes are cyanine dyes, merocyanine dyes and composite merocyanine dyes. For these dyes, any of nuclei which are generally utilized for cyanine dyes may be applied as basic heterocyclic nuclei. Namely, it is possible to apply a pyrroline nucleus, an oxazoline nucleus, a thiazoline nucleus, a pyrrole nucleus, an oxazole nucleus, a thiazole nucleus, a selenazole nucleus, an imidazole nucleus, a tetrazole nucleus and a pyridine nucleus; nuclei wherein alicyclic hydrocarbon rings are fused with the above described nuclei; and nuclei wherein aromatic hydrocarbon rings are fused with the above described nuclei, such as an indolenine nucleus, a benzindolenine nucleus, an indole nucleus, a benzoxazole nucleus, a naphthoxazole nucleus, a benzothiazole nucleus, a naphthothiazole nucleus, a benzoselenazole nucleus, a benzimidazole nucleus or a quinoline nucleus, etc. These nuclei may be substituted on their carbon atoms.

In the merocyanine dyes and the composite merocyanine dyes, it is possible to apply 5 or 6 member heterocyclic nuclei such as a pyrazoline-5-one nucleus, a thiohydantoin nucleus, a 2-thioxazolidine-2,4-dione nucleus, a thiazolidine-2,4-dione nucleus, a rhodanine nucleus or a thiobarbituric acid nucleus, etc. as nuclei having a ketomethylene structure.

Useful sensitizing dyes have been described in, for example, German Patent No. 929,080, U.S. Pat. Nos. 2,231,658, 2,493,748, 2,503,776, 2,519,001, 2,912,329, 3,656,959, 3,672,897 and 3,694,217, British Patent No. 1,242,588 and Japanese Patent Publication No. 14030/69.

Though these sensitizing dyes are used alone, they may be used as a combination of them. The combinations of sensitizing dyes are often used in order to carry out supersensitization. Examples of the combinations have been described in U.S. Pat. Nos. 2,688,545, 2,977,229, 3,397,060, 3,522,052, 3,527,641, 3,617,293, 3,628,964, 3,666,480, 3,679,428, 3,703,377, 3,769,301, 3,814,609 and 3,837,862, British Patent No. 1,344,281 and Japanese Patent Publication No. 4936/68.

Dyes which do not have a spectral sensitization function themselves or substances which do not substantially absorb visible rays but have a supersensitization function may be incorporated in the emulsions together with the sensitizing dyes. For example, the emulsions may contain aminostilbene compounds substituted by nitrogen containing heterocyclic groups (for example, substances described in U.S. Pat. Nos. 2,933,390 and 3,635,721), aromatic organic acid-formaldehyde condensation products (for example, substances described in U.S. Pat. No. 3,743,510), cadmium salts and azaindene compounds, etc. Combination described in U.S. Pat. Nos. 3,615,613, 3,615,641, 3,617,295 and 3,635,721 are particularly preferred.

In the photosensitive materials of the present invention, the hydrophilic colloid layers may contain ultraviolet ray absorbing agents. For example, it is possible to use benzotriazole compounds substituted by aryl groups (for example, compounds described in U.S. Pat. No. 3,533,794), 4-thiazolidone compounds (for example, compounds described in U.S. Pat. Nos. 3,314,794 and 3,352,681), benzophenone compounds (for example, compounds described in Japanese Patent Application (OPI) No. 2784/71), cinnamic acid esters (for example, compounds described in U.S. Pat. Nos. 3,705,805 and 3,707,375) and benzoxazole compounds (for example, compounds described in U.S. Pat. No. 3,499,762). Ultraviolet ray absorbing couplers (for example, α-naphthol type cyan dye forming couplers) or ultraviolet ray absorbing polymers may be used, too. These ultraviolet ray absorbing agents may be mordanted on the specific layer.

The photosensitive materials of the present invention may contain hydroquinone derivatives, aminophenol derivatives, gallic acid derivatives or ascorbic acid derivatives as anti-color-fogging agents. Examples of them have been described in U.S. Pat. Nos. 2,360,290, 2,336,327, 2,403,721, 2,418,613, 2,675,314, 2,701,197, 2,704,713, 2,728,659, 2,732,300 and 2,735,765, Japanese Patent Applications (OPI) Nos. 92988/75, 92989/75, 93928/75 and 110337/75 and Japanese Patent Publication No. 23813/75.

The photographic emulsion layers or other hydrophilic colloid layers in the photosensitive materials the present invention may contain various known surface active agents for various purposes, for example, as coating assistants, for prevention of static charges, for improving the slipping property, for emulsification and dispersion, for prevention of adhesion and for improving photographic characteristics (for example, acceleration of development, hard tone and sensitization), etc.

For example, it is possible to use nonionic surface active agents such as saponin (steroid type), alkylene oxide derivatives (for example, polyethylene glycol, polyethylene glycol/polypropylene glycol condensation products, polyethylene glycol alkyl- or alkyl aryl ethers, polyethylene glycol esters, polyethylene glycol sorbitan esters, polyalkylene glycol alkylamines or amides, and polyethylene oxide addition products of silicones), glycidol derivatives (for example, alkenyl succinic acid polyglycerides and alkylphenol polyglycerides), aliphatic acid esters of polyhydric alcohols, or alkyl esters, urethanes or ethers of sugar, etc.; anionic surface active agents containing acid groups such as a carboxyl group, sulfo group, phospho group, sulfuric acid ester group or phosphoric acid ester group, etc., such as triterpenoid type saponin, alkylcarboxylic acid salts, alkylsulfonic acid salts, alkylbenzenesulfonic acid salts, alkylnaphthalenesulfonic acid salts, alkylsulfuric acid esters, alkyl phosphoric acid esters, N-acyl-N-alkyltaurine, sulfosuccinic acid esters, sulfoalkyl polyoxyethylene alkylphenyl ethers or polyoxyethylene alkyl phosphoric acid esters, etc.; ampholytic surface active agents such as amino acids, aminoalkyl sulfonic acids, aminoalkyl sulfuric or phosphoric acid esters, alkylbetaines, amine imides or amine oxides, etc.; and cationic surface active agents such as alkylamines, aliphatic or aromatic quaternary ammonium salts, heterocyclic quaternary ammonium salts such as pyridinium or imidazolium salts, etc. or aliphatic or heterocyclic phosphonium or sulfonium salts, etc.

Examples of these surface active agents have been described in U.S. Pat. Nos. 2,240,472, 2,831,766, 3,158,484, 3,210,191, 3,294,540 and 3,507,660, British Patents Nos. 1,012,495, 1,022,878, 1,179,290 and 1,198,450, Japanese Patent Application (OPI) No. 117,414/75, U.S. Pat. Nos. 2,739,891, 2,823,123, 3,068,101, 3,415,649, 3,666,478 and 3,756,828, British Patent No. 1,397,218, U.S. Pat. Nos. 3,133,816, 3,441,413, 3,475,174, 3,545,974, 3,726,683 and 3,843,368, Belgium Patent No. 731,126, British Patents Nos. 1,138,514, 1,159,825 and 1,374,780, Japanese Patent Publications Nos. 378/65, 379/65 and 13822/68, U.S. Pat. Nos. 2,271,623, 2,288,226 2,944,900, 3,253,919, 3,671,247, 3,772,021, 3,589,906, 3,666,478 and 3,754,924, German Patent Application (OLS) No. 1,961,638 and Japanese Patent Application (OPI) No. 59025/75, etc.

In the photographic sensitive materials of the present invention, the photographic emulsion layers or other hydrophilic colloid layers may contain inorganic or organic hardening agents. There are, for example, chromium salts (chromium alum or chromium acetate, etc.), aldehydes (formaldehyde, glyoxal or glutaraldehyde, etc.), N-methylol compounds (dimethylol urea or methylol dimethylhydantoin, etc.), dioxane derivatives (2,3-dihydroxydioxane, etc.), active vinyl compounds (1,3,5-triacryloyl-hexahydro-s-triazine or bis-(vinylsulfonyl)-methyl ether, etc.), active halogen compounds (2,4-dichloro-6-hydroxy-s-triazine, etc.), mucohalogenic acids (mucochloric acid or mucophenoxychloric acid, etc.); isoxazoles, dialdehyde starch and 2-chloro-6-hydroxytriazinyl gelatine, etc., which may be used alone or as a combination. Examples of them have been described in U.S. Pat. Nos. 1,870,354, 2,080,019, 2,726,162, 2,870,013, 2,983,611, 2,992,109, 3,047,394, 3,057,723, 3,103,437, 3,321,313, 3,325,287, 3,362,827, 3,539,644 and 3,543,292, British Patents Nos. 676,628, 825,544 and 1,270,578, German Patents Nos. 872,153 and 1,090,427 and Japanese Patent Publications Nos. 7133/59 and 1872/71, etc.

The present invention can be utilized for multilayer multicolor photographic materials comprising at least two layers having each a different spectral sensitivity on a support. The multilayer natural color photographic materials generally have at least one red-sensitive emulsion layer, at least one green-sensitive emulsion layer and at least one blue-sensitive emulsion layer on a support. The order of these layers can be suitably selected as occasion demands. Generally, the red-sensitive emulsion layer contains cyan forming couplers, the green-sensitive emulsion layer contains magenta forming couplers and the blue-sensitive emulsion layer contains yellow forming couplers. However, other combinations may be adopted, if necessary.

In the photographic light-sensitive materials of the present invention, the photographic emulsion layers and other layers are applied to plastic supports generally used for photographic light-sensitive materials, such as plastic films, paper or cloth, etc. or rigid supports such as glass, porcelain or metal, etc. As useful plastic supports, there are films composed of semisynthetic or synthetic high molecular materials such as cellulose nitrate, cellulose acetate, cellulose acetate butyrate, polystyrene, polyvinyl chloride, polyethylene terephthalate or polycarbonate, etc. and paper which is coated with or laminated with barita or α-olefin polymers (for example, polyethylene, polypropylene or ethylene-butene copolymer), etc. The supports may be colored with dyes or pigments. The supports may have a black color for the purpose of intercepting light. The surface of these supports are generally processed so as to form a subbing layer for improving adhesion to photographic emulsion layers. The surface of the supports may be subjected to corona discharging, ultraviolet ray exposure or flame treatment before or after application of the subbing layer.

The photographic emulsions used in the present invention can be produced by processes described in *Chimie et Physique Photographique* written by P. Glafkides (issued by Paul Montel Co., 1967), *Photographic Emulsion Chemistry* written by G. F. Duffin (issued by The Focal Press Co., 1966) and *Making and Coating Photographic Emulsion* written by V. L. Zelikman et al (issued by The Focal Press Co., 1964). Namely, they may be produced by any of acid processes, neutralization processes and ammonia processes. Further, as a process for reacting soluble silver salts with soluble halogen salts, any of one-side mixing process, simultaneous mixing process and combinations of them may be used.

It is possible to use a process which comprises forming particles in the presence of excess silver ion (the so-called reverse mixing process). It is possible to use a process which comprises keeping a pAg of the liquid phase where silver halide is formed to a definite value, the so-called controlled double jet process, as one of the simultaneous mixing processes.

According to this process, silver halide emulsions in which the crystal form is regular and the particle size is nearly uniform can be obtained.

Two or more silver halide emulsions prepared respectively may be mixed.

In the step of formation of silver halide particles or physical ripening, cadmium salts, zinc salts, lead salts, thallium salts, iridium salts or complex salts thereof, rhodium salts or complex salts thereof or iron salts or complex salts thereof may be coexistent.

As the binders or protective colloids for the photographic emulsions, though gelatin is advantageously used, other hydrophilic colloids can be used, too.

For example, it is possible to use proteins such as gelatin derivatives, graft polymers of gelatin with other high molecules, albumin or casein, etc.; sugar derivatives such as cellulose derivatives such as hydroxyethyl cellulose, carboxymethyl cellulose or cellulose sulfate, etc., sodium alginate or starch derivatives, etc. and synthetic hydrophilic high molecular substances such as polyvinyl alcohol, polyvinyl alcohol partial acetal, poly-N-vinyl pyrrolidone, polyacrylic acid, polymethacrylic acid, polyacrylamide, polyvinylimidazole or polyvinylpyrazole, etc. or copolymers thereof.

As the gelatin, it is possible to use not only lime treated gelatin but also acid treated gelatin or enzyme treated gelatin described in *Bull. Soc. Sci. Photo. Japan.* No. 16, page 30 (1966). Further, it is possible to use hydrolysis products or enzymatic products of gelatin. As the gelatin derivatives, it is possible to use substances prepared by reacting gelatin with various compounds such as acid halide, acid anhydride, isocyanates, bromoacetic acid, alkane sultones, vinylsulfonamides, maleinimide compounds, polyalkylene oxides or epoxy compounds, etc. Examples of them have been described in U.S. Pat. Nos. 2,614,928, 3,132,945, 3,186,846 and 3,312,553, British Pat. Nos. 861,414, 1,033,189 and 1,005,784 and Japanese Patent Publication No. 26845/67, etc.

As the above described gelatin-graft polymers, it is possible to use substances prepared by grafting gelatin with homo- or copolymers of vinyl monomers such as acrylic acid, methacrylic acid, ester or amide derivatives of them, acrylonitrile or styrene, etc. It is particularly preferred to use graft polymers of gelatin with polymers having some degree of compatibility with gelatin, such as polymers of acrylic acid, methacrylic acid, acrylamide, methacrylamide or hydroxyalkyl methacrylate, etc. Examples of them have been described in U.S. Pat. Nos. 2,763,625, 2,831,767 and 2,956,884, etc.

Typical synthetic hydrophilic high molecular substances have been described in, for example, German Patent Application (OLS) 2,312,708, U.S. Pat. Nos. 3,620,751 and 3,879,205 and Japanese Patent Publication No. 7561/68.

EXAMPLE 1

To a paper support, both surfaces of which were laminated with polyethylene, the following layers were applied in this order to produce color photosensitive elements.

Table 1

| | |
|---|---|
| The 2nd layer: | Gelatin; coating amount: 1200 $mg/m^2$ |
| The 1st layer: | Silver chlorbromide emulsion (silver bromide; 50 mol%) coating amount: 300 $mg/m^2$ of silver. Cyan coupler (Compound II-I); coating amount: 400 $mg/m^2$. Coupler solvent; coating amount: 200mg/$m^2$. |

As the above described coupler solvent, the following substances were used to produce Samples A–G as the photosensitive elements.

Table 2

| Sample | Coupler Solvent | Remarks |
|---|---|---|
| A | Compound (I - 1) | Present Invention |
| B | Compound (I - 3) | " |
| C | Tricresyl phosphate | Comparison |
| D | Di-n-butyl phthalate | " |
| E | Tri-n-butyl phosphate | " |
| F | Di-(2-ethylhexyl)-n-butyl phosphate | " |
| G | Tri-n-nonyl phosphate | " |

These samples A–G were exposed to light at 1000 lux for 1 second by means of a sensitometer, and they were processed as follows.

| | | | |
|---|---|---|---|
| Processing step: | | | |
| Color Development | 33° C. | 3 minutes and 30 seconds | |
| Bleach-Fix | 33° C. | 1 minute and 30 seconds | |
| Water Wash | 30° C. | 3 minutes | |
| Drying | | | |
| Color Developing Solution: | | | |
| Benzyl Alcohol | | | 15 ml |
| Sodium Sulfite | | | 5 g |
| Potassium Bromide | | | 0.4 g |
| Hydrpxylamine Sulfate | | | 2 g |
| 4-(N-Ethyl-N-β-methanesulfonamido-ethylamino)-2-methylaniline sesquisulfate | | | 6 g |
| Sodium Carbonate (monohydrate) | | | 30 g |
| Water to make | | | 1000 ml |
| | | pH: | 10.1 |
| Bleach-Fix Solution: | | | |
| Ferric salt of ethylenediaminetetra-acetic acid | | | 45 g |
| Sodium Sulfite | | | 10 g |
| 70% Aqueous solution of Ammonium Thiosulfate | | | 160 ml |
| 4 Sodium Ethylenediaminetetraacetate | | | 5 g |
| Water to make | | | 1000 ml |
| | | pH: | 6.8 |

Table 3 shows density decrease ratios (%) to initial densities ($D_{2.0}$ and $D_{1.0}$) of cyan images after the developed Samples A–G were stored in the dark at 60° C. and 75% RH (relative humidity) for 4 weeks and stored under a nearly dry atmosphere at 80° C. for 2 weeks.

Table 3

| | 60° C., 75% RH, 4 weeks | | 80° C., 2 weeks | |
|---|---|---|---|---|
| Sample | $D_{1.0}$ | $D_{2.0}$ | $D_{1.0}$ | $D_{2.0}$ |
| A | 16% | 22% | 20% | 25% |
| B | 15 | 20 | 17 | 24 |
| C | 24 | 36 | 32 | 46 |
| D | 29 | 39 | 38 | 55 |
| E | 24% | 30% | 33% | 39% |
| F | 25 | 32 | 32 | 40 |
| G | 25 | 30 | 30 | 39 |

In Table 3, the lower the density decrease ratio (%) is the better is the fastness to moisture and heat.

According to this experiment, it is understood that cyan images of Samples A and B of the present invention become very fast to heat and moisture as compared with the cases of Samples C and D in which the known coupler solvents are used or the cases of Samples E, F and G in which the number of carbon atoms or the structure of the alkyl group in the coupler solvents is different from that of the coupler solvents of the present invention.

EXAMPLE 2

A solution obtained by dissolving 4.2 g of the cyan coupler (II–I) used in Example 1 in 5 ml of a coupler solvent and 10 ml of ethyl acetate with heating was added to 140 ml of an aqueous solution containing 10 g of gelatin, and the mixture was stirred for 10 minutes by means of a homogenizer. Thus, the coupler and the solvent were finely dispersed. The resulting emulsified dispersion was stored at 5° C. for 4 weeks. The whole of the emulsified dispersion was then heated to 50° C. to dissolve again. It was mixed with 500 g of a photographic emulsion containing $1.04\times10^{-1}$ mols of silver chlorobromide and 40 g of gelatin, and the mixture was filtered using a glass filter. The weight of the residue on the filter was measured and the results shown in Table 4 were obtained.

Table 4

| Coupler Solvent | Residue on Filter | Remarks |
|---|---|---|
| | (mg) | |
| I - 1 | 15 | Present Invention |
| I - 3 | 11 | " |
| Tricresyl phosphate | 262 | Comparison |
| Di-n-butyl phthalate | 760 or more | " |
| Tri-n-butyl phosphate | 73 | |
| Di-(2-ethylhexyl)-n-butyl-phosphate | 34 | " |
| Tri-n-nonyl phosphate | 95 | " |

It is understood from Table 4 that the stability of the emulsified dispersion becomes most excellent when the coupler solvents of the present invention are used, which is very important from the standpoint of preventing trouble at application. Further, it is understood from this experiment that the branched alkyl group in alkyl phosphoric acid esters is important for stability of the emulsified dispersion.

EXAMPLE 3

To a paper support both surfaces of which were laminated with polyethylene, the following 1st layer (the lowest layer) to 6th layer (top layer) were applied in turn to produce color photographic materials (Table 6). As the coupler solvent, the following substances were used to produce Samples H–K.

Table 5

| Sample | Coupler solvent in the 5th layer | Remarks |
|---|---|---|
| H | I - 1 | Present Invention |
| I | I - 3 | " |
| J | Tricresyl phosphate | Comparison |
| K | Di-n-butyl phthalate | " |

These samples were exposed to light at 1000 lux for 1 second by means of a sensitometer and processed by the same manner as in Example 1.

TABLE 6

| |
|---|
| The 6th layer: |
| (Protective Layer) |

TABLE 6-continued

| |
|---|
| Gelatin (amount of application: 1000 mg/m$^2$) |
| The 5th layer: |
| (Red-sensitive layer) |
| Silver chlorobromide emulsion (Br: 50% by mol, amount of application: 300 mg of silver/m$^2$), gelatin (amount of application: 1000 mg/m$^2$), cyan coupler (*1) (amount of application: 400 mg/m$^2$) and coupler solvent (*6) (amount of application: 400 mg/m$^2$) |
| The 4th layer: |
| (Intermediate layer) |
| Gelatin (amount of applicaton: 1200 mg/m$^2$), Ultraviolet ray absorbing agent (*3) (amount of application: 1000 mg/m$^2$) and solvent for ultra violet ray absorbing agent (*2) (amount of application: 250 mg/m$^2$) |
| The 3rd layer: |
| (Green-sensitive layer) |
| Silver chlorobromide emulsion (Br: 50% by mol, amount of application: 290 mg of silver/m$^2$), gelatin (amount of application: 1000 mg/m$^2$), magenta coupler (*4) (amount of application: 200 mg/m$^2$) and coupler solvent (*5) (amount of application: 200 mg/m$^2$) |
| The 2nd layer: |
| (Intermediate layer) |
| Gelatin (amount of application: 1000 mg/m$^2$) |
| The 1st layer: |
| (Blue-sensitive layer) |
| Silver chlorobromide emulsion (Br: 80% by mol, amount of application: 400 mg of silver/m$^2$), gelatin (amount of application: 1200 mg/m$^2$), yellow coupler (*6) (amount of application: 300 mg/m$^2$) and coupler solvent (*7) (amount of application: 150 mg/$^2$) |
| Support: |
| Paper support both surfaces of which were laminated with polyethylene. |

(*1) Coupler: 2-[α-(2,4-di-tert-pentylphenoxy)butanamido]-4,6-dichloro-5-methylphenol (II - 1)
(*2) Solvent: Dibutyl phthalate
(*3) Ultraviolet ray absorbing agent: 2-(2-Hydroxy-3-sec-butyl-5-tert-butylphenyl)-benzotriazole
(*4) Coupler: 1-(2,4,6-Trichlorophenyl)-3-(2-chloro-5-tetradecanamido)anilino-2-pyrazoline-5-one
(*5) Solvent: Tricresyl phosphate
(*6) Coupler: α-Pivaloyl-α-(2,4-dioxy-5,5'-dimethyl-oxazolidine-3-yl)-2-chloro-5-[α-(2,4-ditert-pentylphenoxy)butanamido]acetanilide
(*7) Solvent: Dioctylbutyl phosphate Table 7 shows density decrease ratios (%) to initial densities ($D_{2.0}$ and $D_{1.0}$) of cyan images after the developed Samples H-K were preserved in the dark at 60° C. and 75% RH (relatively humidity) for 4 weeks and preserved under a nearly dry atmosphere at 80° C. for 2 weeks.

Table 7

| Sample | 60° C., 75% RH, 4 weeks | | 80° C., 2 weeks | |
|---|---|---|---|---|
| | $D_{1.0}$ | $D_{2.0}$ | $D_{1.0}$ | $D_{2.0}$ |
| H | 6 | 12 | 13 | 19 |
| I | 6 | 10 | 10 | 18 |
| J | 11 | 24 | 30 | 41 |
| K | 13 | 25 | 35 | 48 |

In Table 7, that the density decrease ratio (%) is lower means that the fastness to moisture and heat is more excellent. In this experiment, it is understood the coupler solvents of the present invention are very effective for preventing fading of cyan images by heat or moisture.

EXAMPLE 4

Acid values of the coupler solvents used for producing Samples A, B, C and D of Example 1 were measured by Japanese Industrial Standard JIS K8004. Further, Samples L, M and N were produced using Compound I-1, Compound I-3 and Compound I-6 which had a particularly low acid value, Sample O was produced with using Compound I-6 which had a somewhat higher acid value, and Sample P was produced with using Compound I-6 which had a high acid value. Acid values were measured according to JIS K8004. The results obtained are shown in Table 8.

Table 8

| Sample | Coupler solvent | Acid Value |
|---|---|---|
| A | Compound I - 1 | 8.4 |
| B | Compound I - 3 | 10.2 |
| C | Tricresyl phosphate | 3.1 |
| D | Di-n-butyl phthalate | 1.5 |
| L | Compound I - 1 | 0.09 |
| M | Compound I - 3 | 0.07 |
| N | Compound I - 6 | 0.12 |
| O | Compound I - 6 | 2.9 |
| P | Compound I - 6 | 11.1 |

Samples A, B, C, D, L, M, N, O and P were subjected to the same development processing and fading test as those in Example 1. The fading property of cyan images of them is shown in density decrease ratios (%) to initial densities in Table 9.

TABLE 8

| Sample | 60° C., 75% RH, 4 weeks | | 80° C., 2 weeks | |
|---|---|---|---|---|
| | $D_{1.0}$ | $D_{2.0}$ | $D_{1.0}$ | $D_{2.0}$ |
| A | 16 | 22 | 20 | 25 |
| B | 15 | 20 | 17 | 24 |
| C | 24 | 36 | 32 | 46 |
| D | 29 | 39 | 38 | 55 |
| L | 8 | 15 | 12 | 16 |
| M | 8 | 13 | 11 | 14 |
| N | 9 14 | 12 | 17 | • |
| O | 12 | 16 | 16 | 19 |
| P | 19 | 24 | 21 | 25 |

It is understood from Table 9 that if compounds represented by General formula (I) having a low acid value are used, the fading property is further improved. On the other hand, if tricresyl phosphate and di-n-butyl phthalate which are beyond the scope of the present invention are used, fading in the dark is not good, even though the acid value is low.

While the invention has been described in detail and with reference to specific embodiments thereof, it will be apparent to one skilled in the art that various changes and modifications can be made therein without departing from the spirit and scope thereof.

What is claimed is:

1. Silver halide color photographic light-sensitive materials comprising a support and at least one silver halide emulsion layer on said support, wherein at least one of said emulsion layers contains a hydrophobic phenol type or napthol type cyan dye forming coupler and at least one coupler solvent represented by the following general formula (I):

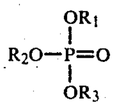

(I)

wherein $R_1$, $R_2$ and $R_3$ represent each a branched chain alkyl group containing 8 or more carbon atoms and may be the same or different from one another, provided the sum total of carbon atoms in the compound is 24 to 40.

2. The light-sensitive material of claim 1 wherein $R_1$, $R_2$ and $R_3$ each has 8 to 10 carbon atoms.

3. The light-sensitive material of claim 1, wherein the cyan coupler is represented by the formula (II) or (III)

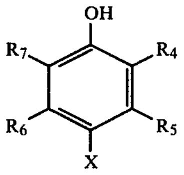

(II)

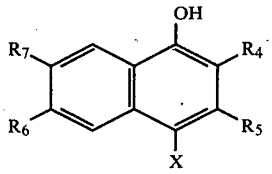

(III)

wherein $R_4$ represents a hydrogen atom, an aliphatic group, an alkoxy group, an aryloxy group, an acylamido group, a sulfonamido group, an acid amide group or a carbamoyl group; and $R_5$, $R_6$ and $R_7$ represent a hydrogen atom, a halogen atom, an alkyl group, an aryl group, an alkoxy group, an alkylthio group, a heterocyclic group, an amino group, a carbonamido group, a sulfonamido group, a sulfamoyl group or a carbamoyl group; and X represents a hydrogen atom or a group which is released upon coupling.

4. The light-sensitive material of claim 1, wherein the ratio by weight of branched chain alkyl phosphoric acid esters to cyan couplers is 0.1 to 2.

5. The light-sensitive material of claim 3, wherein said cyan coupler is represented by the formula (II).

6. The light-sensitive material of claim 1, wherein the branched chain alkyl phosphoric acid ester is tri-(2-ethylhexyl)phosphate.

7. The light-sensitive material of claim 1, wherein the branched chain alkyl phosphoric acid ester is tri-(3,5,5-trimethylhexyl)phosphate.

8. The light-sensitive material of claim 1, wherein the cyan coupler is 2-[α-(2,4-di-tert-pentylphenoxy)-butanamido]-4,6-dichloro-5-methylphenol.

9. The light-sensitive material of claim 1, wherein the acid value of the coupler solvent represented by the general formula (I) is 5 or less.

10. The light-sensitive material of claim 1, wherein the acid value of the coupler solvent represented by the general formula (I) is 1 or less.

11. The light-sensitive material of claim 1, wherein the acid value of the coupler solvent represented by the general formula (I) is 0.1 or less.

12. The light-sensitive material of claim 3, wherein said group which is released upon coupling is selected from the class consisting of a halogen atom, a thiocyano group, an acyloxy group, an alkoxy group, an aryloxy group or a cyclic imide group.

* * * * *